(12) United States Patent
Sacchetti et al.

(10) Patent No.: US 9,993,392 B2
(45) Date of Patent: *Jun. 12, 2018

(54) ENTERAL FEEDING PUMP SYSTEM

(71) Applicant: Alcor Scientific, Inc., Smithfield, RI (US)

(72) Inventors: Peter J. Sacchetti, Attleboro, MA (US); Ralph Beckman, Providence, RI (US)

(73) Assignee: ALCOR SCIENTIFIC INC., Smithfield, RI (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/979,267

(22) Filed: Dec. 22, 2015

(65) Prior Publication Data
US 2016/0346169 A1 Dec. 1, 2016

Related U.S. Application Data

(60) Division of application No. 13/731,048, filed on Dec. 30, 2012, now Pat. No. 9,233,053, which is a
(Continued)

(51) Int. Cl.
*A61J 15/00* (2006.01)
*A61M 5/142* (2006.01)
(Continued)

(52) U.S. Cl.
CPC ....... *A61J 15/0076* (2015.05); *A61J 15/0011* (2013.01); *A61M 5/14212* (2013.01);
(Continued)

(58) Field of Classification Search
CPC .... A61J 15/0011; A61J 15/0076; A61J 9/005; A61M 2202/0482; A61M 39/08;
(Continued)

(56) References Cited

U.S. PATENT DOCUMENTS 1,856,350 A 5/1932 Metcalf
2,318,721 A 5/1943 Siver
(Continued)

*Primary Examiner* — Bhisma Mehta
*Assistant Examiner* — Brandy S Lee
(74) *Attorney, Agent, or Firm* — Adler Pollock & Sheehan P.C.; Daniel J. Holmander, Esq.

(57) ABSTRACT

An enteral pump system for delivering medical fluids unidirectionally includes a disposable fluid delivery set having a repeatable compression portion and an enteral feeding pump. The repeatable compression portion is helically coiled around a central axis to define a cylindrical shape. The compression portion is configured to pump a large volume of medical fluids per stroke. The compressing portion includes at least two adjacent tubing walls joined around the central axis for repeatable compression. The enteral feeding pump is configured to repeatedly and reliably compress the compression portion of the fluid delivery set along the central axis. In operation, the compression portion is repeatably compressed without distortion along the central axis by the enteral feeding pump to flow unidirectionally through the fluid delivery set.

4 Claims, 12 Drawing Sheets

Related U.S. Application Data continuation-in-part of application No. 12/488,460, filed on Jun. 19, 2009, now Pat. No. 8,449,501.

(60) Provisional application No. 61/073,964, filed on Jun. 19, 2008.

(51) Int. Cl.
*A61M 39/08* (2006.01)
*A61M 5/168* (2006.01)
*B65H 54/04* (2006.01)
*B65H 75/28* (2006.01)
*A61J 9/00* (2006.01)

(52) U.S. Cl.
CPC .... *A61M 5/14228* (2013.01); *A61M 5/16881* (2013.01); *A61M 39/08* (2013.01); *B65H 54/04* (2013.01); *B65H 75/28* (2013.01); *A61J 9/005* (2013.01); *A61M 2202/0482* (2013.01); *B65H 2701/33* (2013.01)

(58) Field of Classification Search
CPC .......... A61M 5/14212; A61M 5/14228; A61M 5/16881; B65H 2701/33; B65H 54/04; B65H 75/28
See application file for complete search history.

(56) References Cited

U.S. PATENT DOCUMENTS

| | | | |
|---|---|---|---|
| 2,377,170 A * | 5/1945 | Morgan | B60G 17/04 137/598 |
| 2,387,215 A | 10/1945 | Fawkes | |
| 2,602,764 A | 7/1952 | Billingham | |
| 3,554,224 A | 1/1971 | Kirk et al. | |
| 3,685,532 A | 8/1972 | Kasschau | |
| 3,720,221 A | 3/1973 | Hufeld et al. | |
| 3,853,145 A | 12/1974 | Judd | |
| 4,016,897 A | 4/1977 | Asioli | |
| 4,116,216 A | 9/1978 | Rosenberg | |
| 4,173,233 A | 11/1979 | Snyder | |
| 4,178,963 A | 12/1979 | Riefler et al. | |
| 4,221,238 A | 9/1980 | Madsen | |
| 4,276,333 A | 6/1981 | Cobean | |
| D287,044 S | 12/1986 | Hughes | |
| 4,632,361 A | 12/1986 | Callison | |
| 4,673,397 A | 6/1987 | Lynn et al. | |
| 4,710,166 A | 12/1987 | Thompson et al. | |
| 4,718,896 A | 1/1988 | Arndt et al. | |
| 4,729,406 A | 3/1988 | Frentzel | |
| 4,820,265 A | 4/1989 | DeSatnick et al. | |
| 4,845,487 A | 7/1989 | Frantz et al. | |
| 5,022,426 A | 6/1991 | Fischer | |
| 5,209,654 A | 5/1993 | Lofsjogard et al. | |
| 5,408,990 A | 4/1995 | Edling et al. | |
| 5,458,578 A | 10/1995 | Sebesta et al. | |
| 5,514,102 A | 5/1996 | Winterer et al. | |
| 5,810,770 A | 9/1998 | Chin et al. | |
| 5,958,167 A | 9/1999 | Van Driel et al. | |
| 5,964,580 A | 10/1999 | Taga | |
| 6,128,884 A | 10/2000 | Berdan, II et al. | |
| 6,607,368 B1 | 8/2003 | Ross et al. | |
| 6,622,933 B1 | 9/2003 | Young et al. | |
| 6,626,329 B2 | 9/2003 | Rake et al. | |
| 8,137,541 B2 | 3/2012 | Zook | |
| D667,350 S | 9/2012 | Smith | |
| 9,233,053 B2 * | 1/2016 | Sacchetti | A61M 5/14228 |
| 2001/0044603 A1 | 11/2001 | Harrold | |
| 2004/0026525 A1 | 2/2004 | Fiedrich | |
| 2004/0108333 A1 | 6/2004 | Rake et al. | |
| 2005/0209563 A1 | 9/2005 | Hopping et al. | |
| 2007/0107364 A1 | 5/2007 | Estes et al. | |
| 2008/0051697 A1* | 2/2008 | Mounce | A61M 5/1413 604/32 |
| 2009/0019802 A1 | 1/2009 | Crall, Jr. | |
| 2009/0199915 A1 | 8/2009 | Novacek et al. | |
| 2009/0229692 A1 | 9/2009 | Rohwer et al. | |
| 2012/0096785 A1 | 4/2012 | Weeks | |

\* cited by examiner

ENTERAL FEEDING PUMP SYSTEM

CROSS REFERENCE TO RELATED APPLICATIONS

This application is a divisional application related to and claims priority from earlier filed Non-Provisional patent application Ser. No. 13/731,048 filed Dec. 30, 2012 which is a continuation application from earlier filed Non-Provisional patent application Ser. No. 12/488,460 filed Jun. 19, 2009, now U.S. Pat. No. 8,449,501 and earlier filed provisional patent application Ser. No. 61/073,964 filed Jun. 19, 2008, the entire contents of which are incorporated herein by reference.

BACKGROUND OF THE INVENTION

The invention generally relates to enteral feeding systems, and in particular enteral feeding pump systems. More specifically, the invention relates to an enteral feeding pump system for delivering medical fluids unidirectionally including a disposable fluid delivery set having a repeatable compression portion which is helically coiled to define a cylindrical shape. The compression portion pumps a large volume of medical fluids per stroke. Also, an enteral feeding pump configured to repeatedly and reliably compress the compression portion of the fluid delivery set along a central axis.

Enteral feeding pump systems are used to supply fluid nutrition to patients who are unable to eat. The pumping system consists of the pump and disposable tubing sets. It is well known in the art that pumping action for an enteral feeding pump system has been primarily achieved by rotary peristaltic and linear peristaltic systems.

The rotary peristaltic system is a common approach that requires the use of a fluid delivery set having an elastomeric tubing segment in contact with rotating rollers of a rotary peristaltic pump. The elastomeric tubing segment is typically made of silicone rubber because of its good durability. The use of this material also requires transitional hardware to connect to the lower cost PVC tubing of the fluid delivery set which are used to convey the fluids from a source container to a patient. The tubing segment made of silicone rubber and associated hardware add significant costs to the rotary peristaltic systems.

Another common enteral feeding pump system is a linear peristaltic system. The linear peristaltic system requires tubing that is compressed in a series of platens. The tubing required for the linear peristaltic pump is usually a higher grade (softer) PVC different from the low-grade PVC tubing used to convey fluid from a source container to a patient. The compression in the linear peristaltic system generates a unidirectional fluid flow that is controlled by the rate of the compression steps. The pumped volume per stroke for this approach is typically very small so that a relatively large number of compressions are required to meet flow demand and mechanical pumping components are stressed.

Therefore, there remains a need in the prior art for an enteral feeding pump system that provides for delivering medical fluids unidirectionally including a disposable fluid delivery set having a repeatable compression portion capable of pumping a large volume of fluids per stroke and an enteral feeding pump configured to repeatedly and reliably compress the compression portion of the fluid delivery set along a central axis. In addition, there is a need for compression in an enteral feeding pump system using lower cost and, preferably, lower grade tubing. Also, there is a need for an enteral feeding pump system that does not require transitional hardware to reduce the overall cost of the enteral pumping system. Also, there is a need for an enteral feeding system that requires less compressions to meet flow demand and does not stress other mechanical components.

BRIEF SUMMARY OF THE INVENTION

The invention preserves the advantages of prior enteral feeding pump systems. In addition, it provides new advantages not found in currently available enteral feeding pump systems and overcomes many disadvantages of such currently available enteral feeding pump systems. The present invention provides an enteral feeding pump system for delivering medical fluids unidirectionally including a disposable fluid delivery set having a repeatable compression portion capable of pumping a large volume of fluids per stroke and an enteral feeding pump configured to repeatedly and reliably compress the compression portion of the fluid delivery set along a central axis.

An enteral pump system for delivering medical fluids unidirectionally includes a disposable fluid delivery set having a repeatable compression portion and an enteral feeding pump. The disposable fluid delivery set including a disposable tubing having a source end and a patient end used for providing nutritional fluids to a patient. In one embodiment, the disposable tubing is a low grade tubing throughout its entire length. For example, the low grade tubing may be a low-grade PVC (polyvinyl chloride) tubing or other inexpensive tubing approved for use in the medical field.

The compression portion is configured to pump a large volume of medical fluids per stroke from a source end to a patient end relative to other prior art enteral feeding pump systems. The repeatable compression portion of the fluid delivery set is helically coiled to define a cylindrical shape. The compressing portion includes at least two adjacent tubing walls joined along a central axis for repeatable central compression. The adjacent tubing walls are joined at wall contact points where at least two adjacent tubing walls meet at a central portion of the adjacent tubing walls. In one embodiment, the adjacent tubing walls are joined at said wall contact points using a solvent material to prevent distortion of the compression portion during repeated central compression.

The disposable fluid delivery set including the compression portion of the tubing may be a spike set, bag set, or other configurations. The spike set may include a spike member fluidly connected at the source end of the tubing, one or more roller clamp members positioned along said tubing, and a patient fitting fluidly connected to the patient end. The bag set may include a bag fluidly connected at the source end of the tubing, one or more roller clamp members positioned along the tubing, a drip chamber fluidly connected with the tubing near the bag, and a patient fitting fluidly connected to the patient end of the tubing. Other configurations or variations of the spike set and bag set may be used by adding or removing components to the fluid delivery set.

The enteral feeding pump is configured to repeatedly and reliably compress the compression portion of the fluid delivery set along a central axis. The enteral feeding pump including a housing, a pump motor unit disposed within the housing, a controller disposed within the housing for directing the operation of the pump motor unit to provide selective sequential compression, a repeatable compression means for compressing the compression portion of the fluid delivery set.

In one embodiment, the repeatable compression means includes a plate system driven by the pump motor unit and disposed within the housing. The plate system includes a top plate respectively positioned to a bottom plate. The top plate and the bottom plate configured to receive the compression portion of a fluid delivery set. The top plate operationally connected to the motor unit to move the top plate along an axis towards the bottom plate.

The enteral feeding pump may also include a regulation means for regulating the flow of medical fluid into and out of the compression portion of the fluid delivery set. In one embodiment, the means for regulating a flow of medical fluid are source end and patient end pinching mechanisms disposed within the housing and operationally connected to the pump motor unit. The source end pinching mechanism includes first source end and second source end pinching members. The first source end pinching member respectively positioned to the second source end pinching member. The first source end and second source end pinching members configured to receive a portion of a fluid delivery set between said source end of the fluid delivery set and the compression portion of said fluid delivery set. The first source end pinching member, second source end pinching member, or both operationally connected to the motor unit to move the first source end pinching member relatively towards said second source end pinching member to regulate the flow of fluid through the fluid delivery set from a fluid source.

The patient end pinching mechanism includes first patient end and second patient end pinching members. The first patient end pinching member respectively positioned to the second patient end pinching member. The first patient end and second patient end pinching members configured to receive a portion of the fluid delivery set between the patient end of the fluid delivery set and the compression portion of the fluid delivery set. The first patient end pinching members operationally connected to the motor unit to move the first patient end pinching member relatively towards the second patient pinching members to regulate the flow of fluid through the fluid delivery set and to the patient.

In another embodiment, the means for regulating a flow of medical fluid into and out of the compression portion of the fluid delivery set includes two or more valves connected at a patient end and source end of the fluid delivery set. For example, a source end one-way valve is fluidly connected between the source end and the compression portion of the fluid delivery set. In addition, a patient end one-way valve fluidly connected between the patient end and the compression portion of the fluid delivery set. The valves are preferably one-way valves or other valves which allow fluid to flow unidirectionally.

In operation, the compression portion is repeatably compressed without distortion along a central axis by the enteral feeding pump to flow fluid unidirectionally through the fluid delivery set using selective sequential compression. For example, when the patient end pinching mechanism is in an open position, the compression portion is compressed or stroked into a compression position to allow the fluid to flow out of the compression portion and through the patient end. Next, the patient end pinching mechanism is in a closed position and the source end pinching mechanism is in an open position. The compression portion then rebounds from the compressed position to draw fluid through the source end and into the compression portion. Note, this selective sequential compression may be adjusted using different predetermined timing sequences to increase or decrease the desired flow rate and volume of fluid delivered to the patient.

The invention also includes a method for flowing fluid unidirectionally using an enteral pumping system including a disposable fluid delivery set and enteral feeding pump for delivery medical fluids. The method includes the following steps. First, a fluid delivery set is provided which includes a source end, a patient end, and the repeatable compression portion. Second, the enteral feeding pump is provided for repeatable compressing of the compression portion and regulating the flow of fluid into and out of the compression portion. Third, the fluid delivery set is inserted into the enteral feeding pump. Fourth, the repeatable compression portion of the fluid delivery set is compressed using the enteral feeding pump. Fifth, a regulating means closes the flow of medical fluid out of the compression portion and into the patient end using the enteral feeding pump. Sixth, a regulating means opens the flow of medical fluid into the compression portion from the source end using the enteral feeding pump. Seventh, the compressed portion is released using the enteral feeding pump to allow medical fluids to be drawn into the fluid delivery set through the regulating means and into the compression portion from the source end. Eighth, the regulating means closes the flow of medical fluid into the compression portion from the source end using the enteral feeding pump. Ninth, the compressing portion is compressed by the enteral feeding pump to move medical fluids out of the compression portion, through the regulating means, and into the patient end. This process is continued depending upon the flow rate and volume of liquid desired for a patient.

The present invention also includes a method of manufacture of a repeatable compression portion of a disposable fluid delivery set. The compression portion of a disposable fluid delivery set may be produced by the following steps. First, a disposable tubing is provided that is used for medical purposes. Second, the tubing is helically coiled around a central axis to define a cylindrical shape. Third, the tubing is tensioned during coiling to provide at least two adjacent tubing walls around the central axis for repeatable compression. Fourth, a dispensing solvent is applied at wall contact points where at least two adjacent tubing walls meet at a central portion of said adjacent tubing walls to join adjacent tubing walls during coiling. Fifth, the tubing is coiled under tension and joined by dispensing solvent to join adjacent tubing walls until desired number of coil turns is reached to define a cylindrical shape of the compression portion of the fluid delivery set. The number of turns for the compression portion is variable depending upon the desire volume displaced upon a stroke.

The invention also includes a coiling apparatus for producing a repeatable compression portion of a disposable fluid delivery set. The coiling apparatus includes a spinning mandrel and a solvent dispenser. The mandrel and solvent dispenser having a power source, a motor unit for turning the mandrel, a controller for directing the operation of the motor unit and controller, and a solvent source. The mandrel is configured for helically coiling a disposable tubing under controlled tension to produce a compression portion of the tubing defining a cylindrical shape. The mandrel includes a retaining means for the tubing on the mandrel during coiling. A solvent dispenser is positioned near said mandrel to contact the compression portion of the tubing. The dispenser is in fluid connection with a solvent source. The dispenser providing a solvent to join wall contact points of adjacent tubing walls of the compression portion during helical coiling of the tubing.

In another embodiment, a repeatable compression portion of the tubing set may be formed in an alternative manner. A capture mechanism of an enteral feeding pump may provide a repeatable compression portion of the tubing set. The capture mechanism has a housing with one or more apertures for initial receipt a straight or linear portion of the tubing set. A reeling mechanism is connected within the housing and operationally connected to the enteral feeding pump for control of operations. The reeling mechanism has an inner area and an outer area. The reeling mechanism has one or more apertures within the outer area for initial receipt of the portion of the tubing set. The inner area defines a channel for receipt of the portion of the tubing set to secure the tubing set within the capture mechanism. The reeling mechanism is configured to rotate about an axis. When it rotates, the reeling mechanism provides the repeatable compression portion by helically coiling the portion of the tubing set about an central axis.

It is therefore an object of the invention to provide an enteral feeding pump system including a fluid delivery set and enteral feeding pump for delivering fluid unidirectionally.

It is another object of the invention to provide a fluid delivery set including low-grade or inexpensive tubing that has a repeatable compression portion.

It is another object of the invention to provide a spike set and bag set for fluid delivery in enteral feeding that includes a repeatable compression portion.

It is an object of the invention to provide the compression portion of the fluid delivery set which pumps a large volume of medical fluids per stroke.

It is yet another object of the invention to provide an enteral feeding pump configured to repeatedly and reliably compress the compression portion of the fluid delivery set.

It is a further object of the invention to provide compression in an enteral feeding pump system using lower cost tubing.

Another object of the invention is to provide an enteral feeding pump system that requires less hardware to reduce the overall cost of the enteral pumping system.

A further object of invention is to provide an enteral feeding pump system that requires less compressions to meet flow demand and does not stress other mechanical components.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawings in which:

DETAILED DESCRIPTION OF THE PREFERRED EMBODIMENTS

Figure 1:
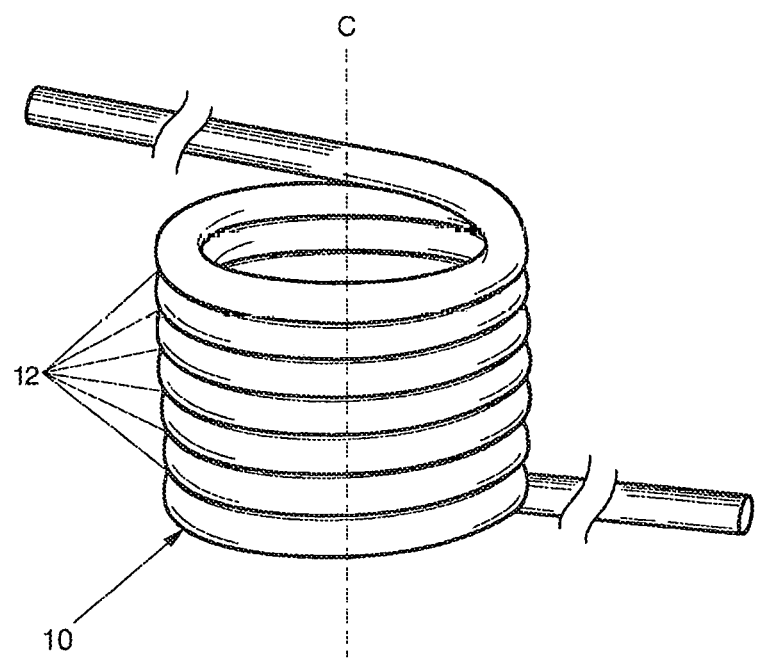
FIG. 1 is a perspective view of a compression portion of a disposable fluid delivery set.

In accordance with the invention of FIGS. 1-10, the invention generally relates to enteral feeding systems, and in particular enteral feeding pump systems. More specifically, the invention relates to an enteral feeding pump system for delivering medical fluids unidirectionally including a disposable fluid delivery set having a repeatable compression portion which is helically coiled to define a cylindrical shape. The compression portion pumps a large volume of medical fluids per stroke. Also, an enteral feeding pump configured to repeatedly and reliably compress the compression portion of the fluid delivery set along a central axis.

Referring to FIGS. 1-7, an enteral pump feeding system 60, 70 for delivering medical fluids unidirectionally includes a disposable or replaceable fluid delivery set 20, 30 having a repeatable compression portion 10 and an enteral feeding pump 40. The disposable fluid delivery set 20, 30 is configured for engaging with an enteral feeding pump 40. The disposable fluid delivery set 20, 30 including a disposable tubing 21, 31 having a source end 21B, 31B for connection to a nutritional source and a patient end 21A, 31A for connection to a patient. The disposable tubing 21, 31 has a tubing wall and an area defined therein for the flow of fluid.

In one embodiment, the disposable tubing 21, 31 is a low grade tubing throughout its entire length. For example, the low grade tubing may be a low-grade PVC (polyvinyl chloride) tubing or other inexpensive tubing approved for use in the medical field. It should be noted that this invention is not limited to low-grade PVC tubing and that any tubing used in the medical field may be used, preferably inexpensive tubing. Low-grade PVC tubing is typically the standard tubing set used today in existing enteral feeding pump systems. The use of the low-grade PVC tubing set saves additional costs over using more expensive higher grade PVC tubing sets, especially tubing sets using silicone portions.

The compression portion 10 is configured to repeatably pump a large volume of medical fluids per stroke from a source end 21B, 31B to a patient end 21A, 31A. The compression portion 10 is durable and able to weather repeated compression over a longer period of time. The repeatable compression portion 10 of the fluid delivery set 20, 30 is helically coiled around a central C or vertical axis to define a cylindrical shape. Of course, other shapes are capable of displacing a large volume of fluid, such as coiled and spiral shapes. The compressing portion 10 includes at least two adjacent tubing walls joined or stacked around a central axis C for repeatable axial compression along the central axis C. The adjacent tubing walls are joined at wall contact points 12 where at least two adjacent tubing walls meet at a central portion of the adjacent tubing walls. In one embodiment, the adjacent tubing walls are joined at said wall contact points 12 using a solvent material to prevent distortion of the compression portion 10 during repeated compression.

The compression section 10 may have an adjustable number of coil turns. The number of coil turns, diameter of the tubing, and the diameter of the compression section is variable depending upon the desired volume of liquid stroked or displaced, the flow rate, type of tubing material, durometer of the tubing material, viscosity of the fluid, and other compression factors. For example, FIG. 1 illustrates a compression section 10 with seven coil turns. In another embodiment, the number of coil turns for the compression portion 10 may be seven with an inner diameter of 25 mm for the compression portion 10. In another example, the number of coil for the compression section 10 may be nine with an inner diameter of 0.916 inches for the compression portion 10. These are only examples and the number of coil turns and inner diameter may be adjusted according to desired characteristics discussed above.

Figure 2:
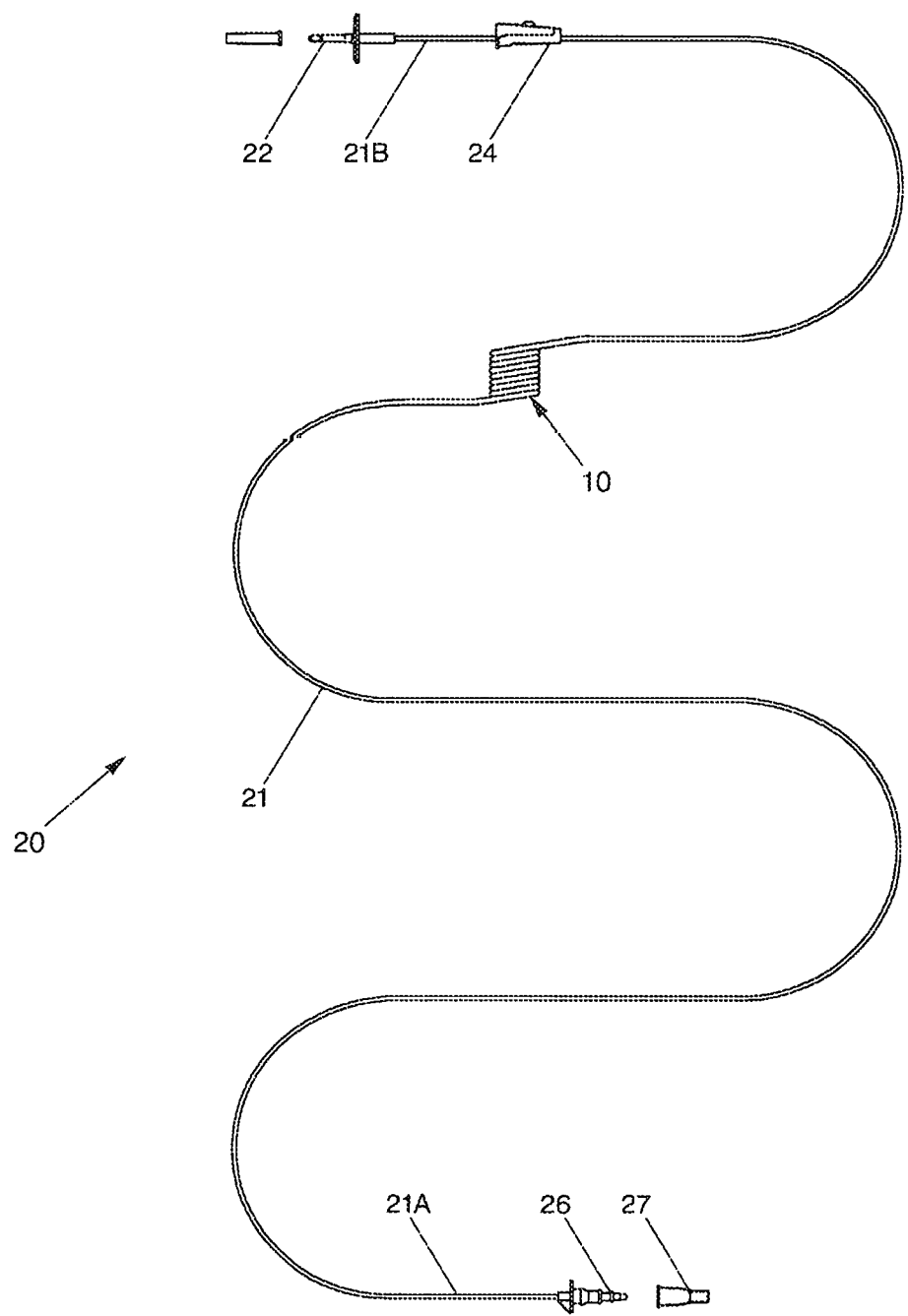
FIG. 2 is a plan view of a disposable fluid delivery set including a compression portion and a spike member.
Figure 3:
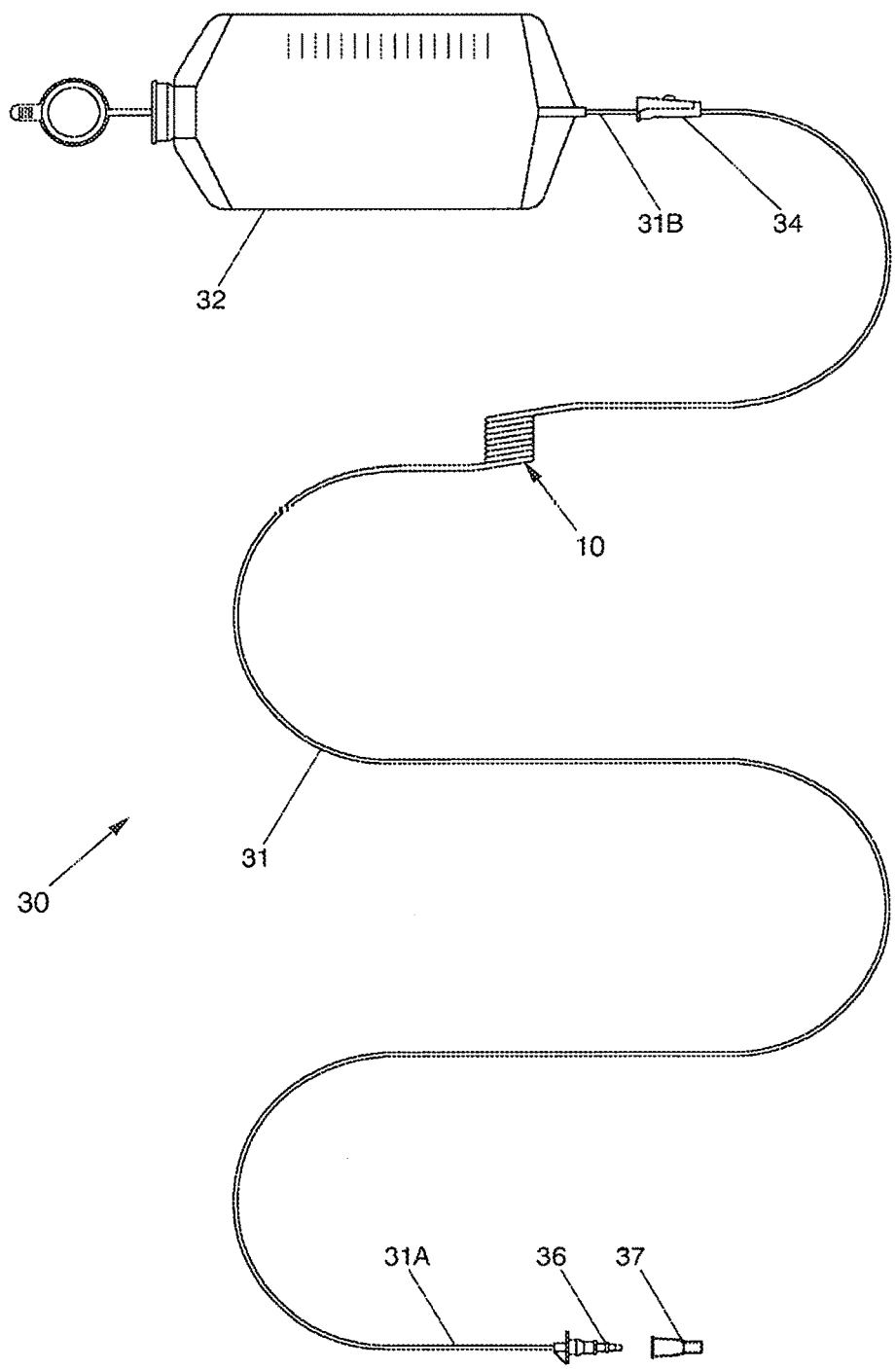
FIG. 3 is a plan view of a disposable fluid delivery set including a compression portion and a bag.

Referring to FIGS. 2-3, the remainder of the fluid delivery set 20, 30 at each end of the compression section 10 is used to connect to the fluid source and the patient. The remainder of the disposable fluid delivery 20, 30 set may include a spike set 20, bag set 30, or other configurations. The spike set 20 may include a spike member 22 fluidly connected at the source end 21B of the tubing 21, one or more roller clamp members 24 positioned along the tubing 21, and a patient fitting 26 with a cap 27 fluidly connected at the patient end 21A. The bag set 30 may include a bag 32 fluidly connected at the source end 31B of the tubing 31, one or more roller clamp members 34 positioned along the tubing 31, a drip chamber (not shown) fluidly connected with the tubing 31 near the bag 32, and a patient fitting 36 with a cap 37 fluidly connected to the patient end 31A of the tubing 31. Other configurations or variations of the spike set 20 and bag set 30 may be used by adding or removing components to the fluid delivery sets 20, 30.

Figure 4:
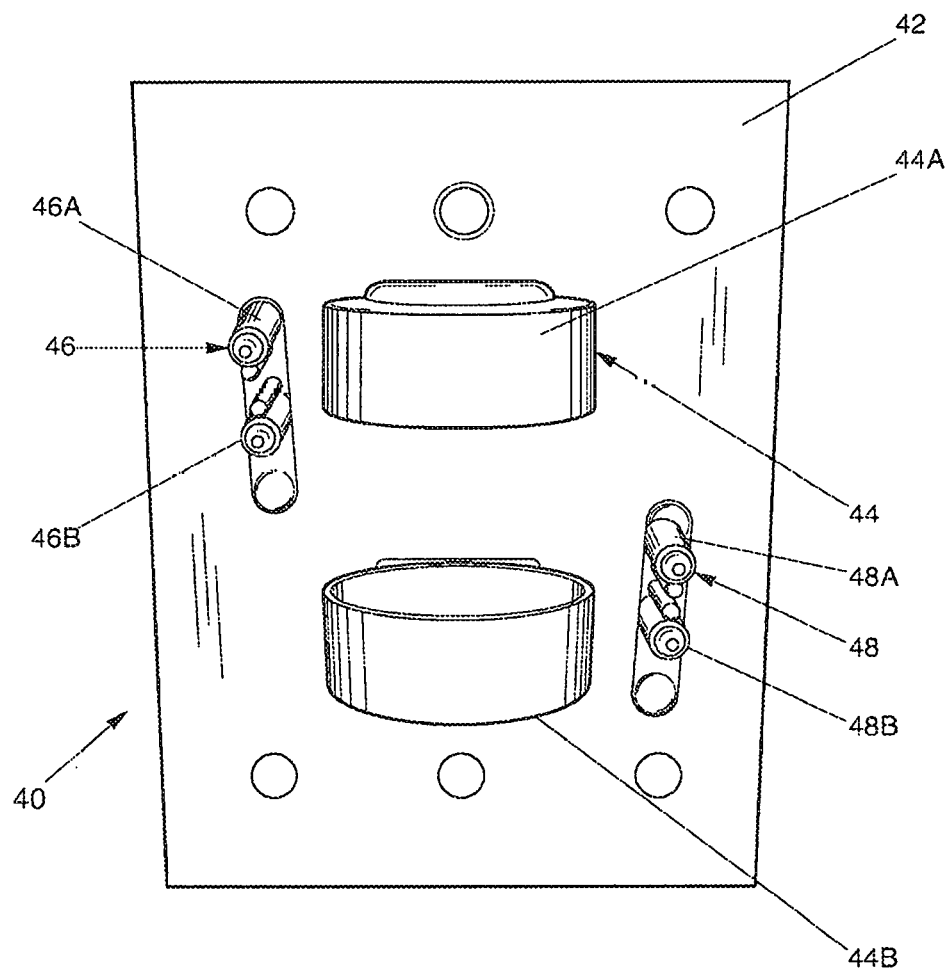
FIG. 4 is a front view of an enteral feeding pump for delivering medical fluids.
Figure 5:
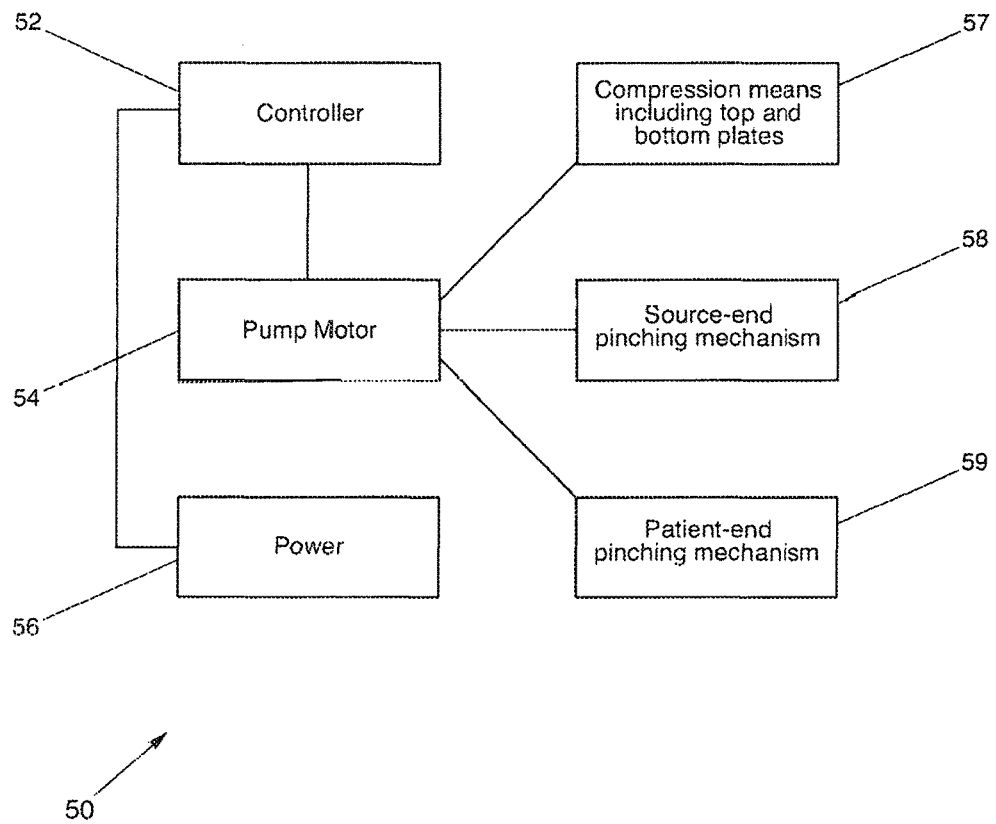
FIG. 5 is a block diagram of the operational components of the enteral feeding pump of FIG. 4.
Figure 6:
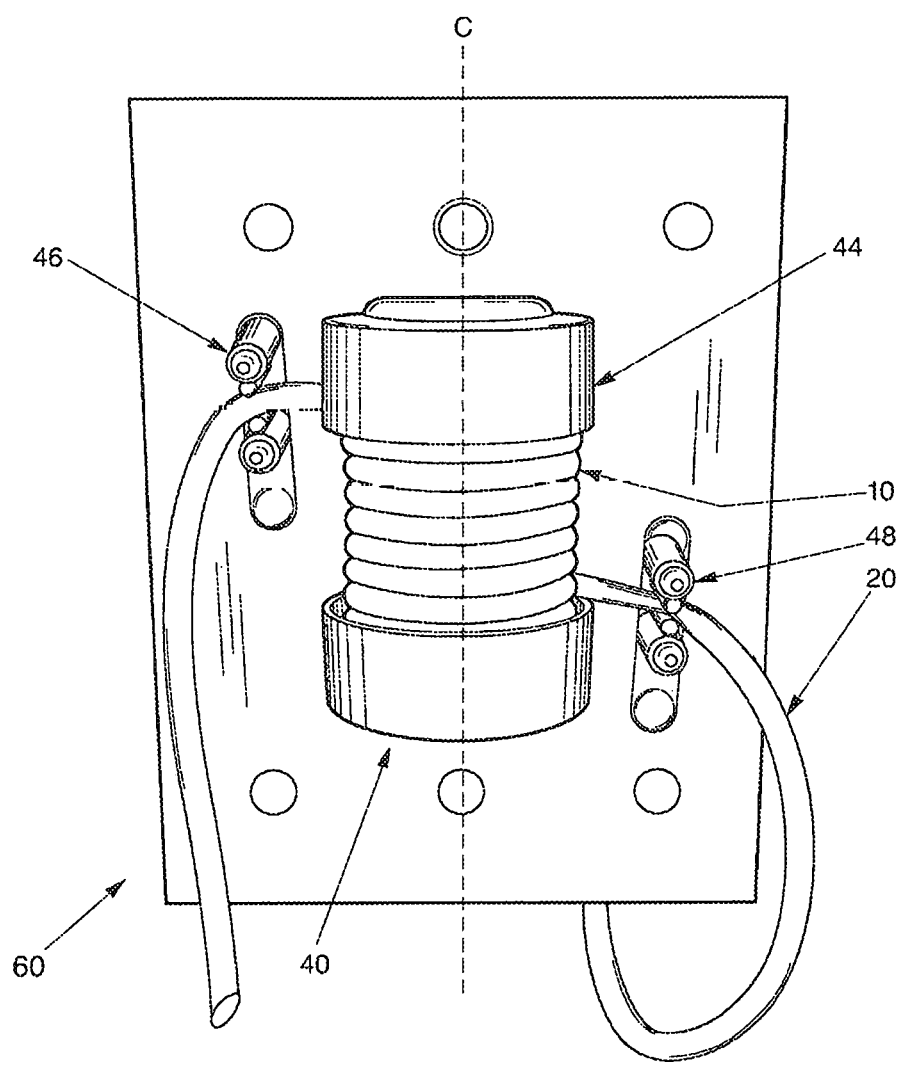
FIG. 6 is a front view of an enteral feeding pump system including an enteral feeding pump and disposable fluid delivery set including a compression portion.
Figure 7:
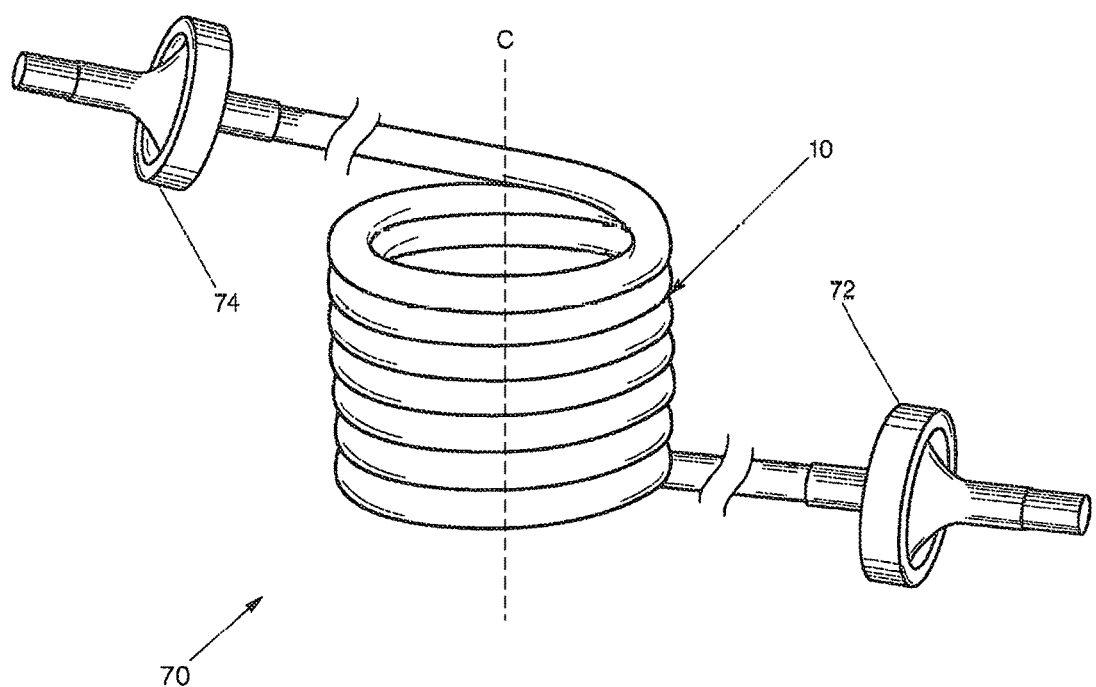
FIG. 7 is a front view of a enteral feeding pump system including a disposable fluid delivery set including a compression portion and one-way valves.
Figure 8:
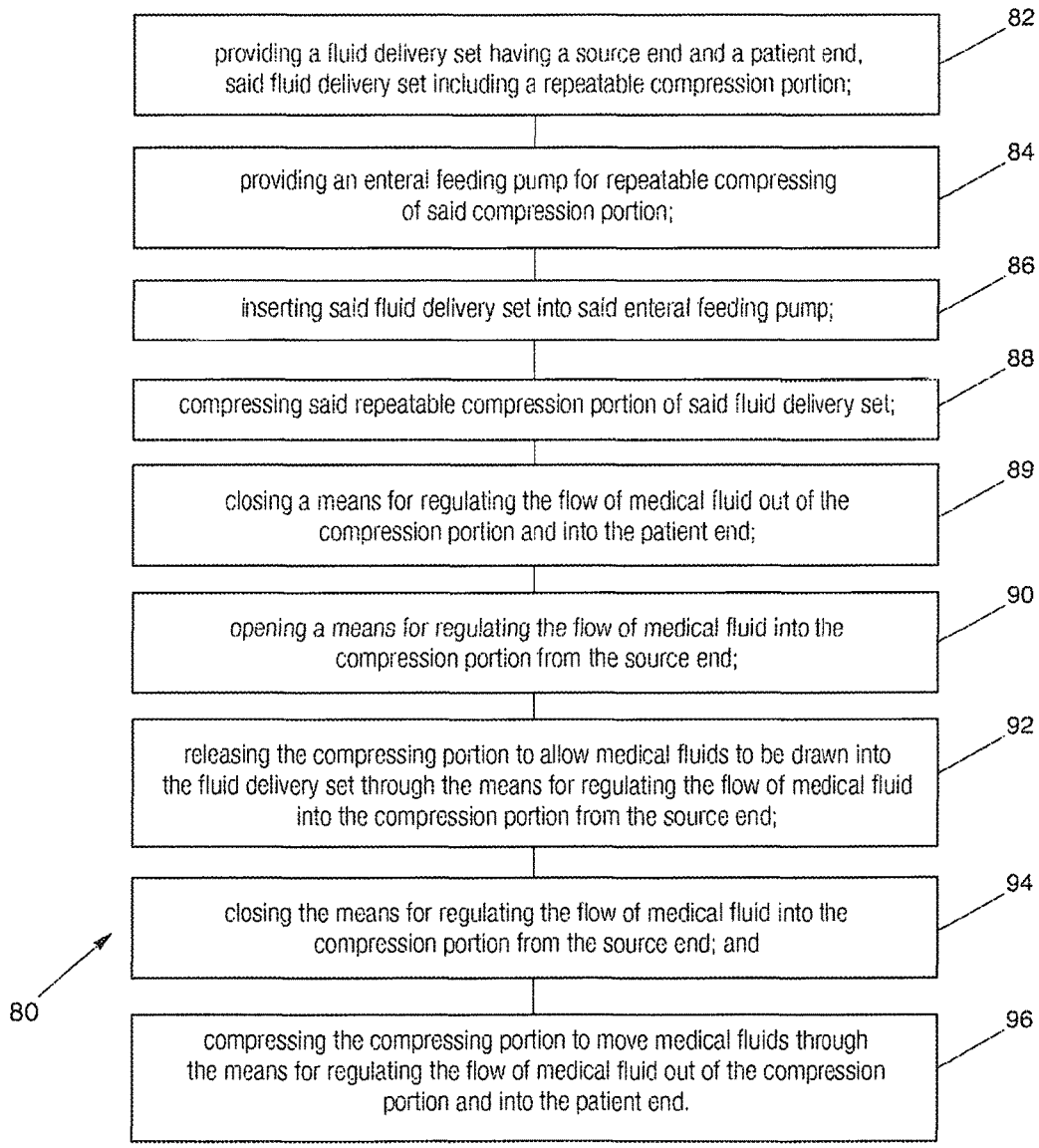
FIG. 8 is a block diagram of a method for flowing fluid unidirectionally using an enteral pumping system including an enteral feeding pump and disposable fluid delivery set having a compression portion.
Figure 9:
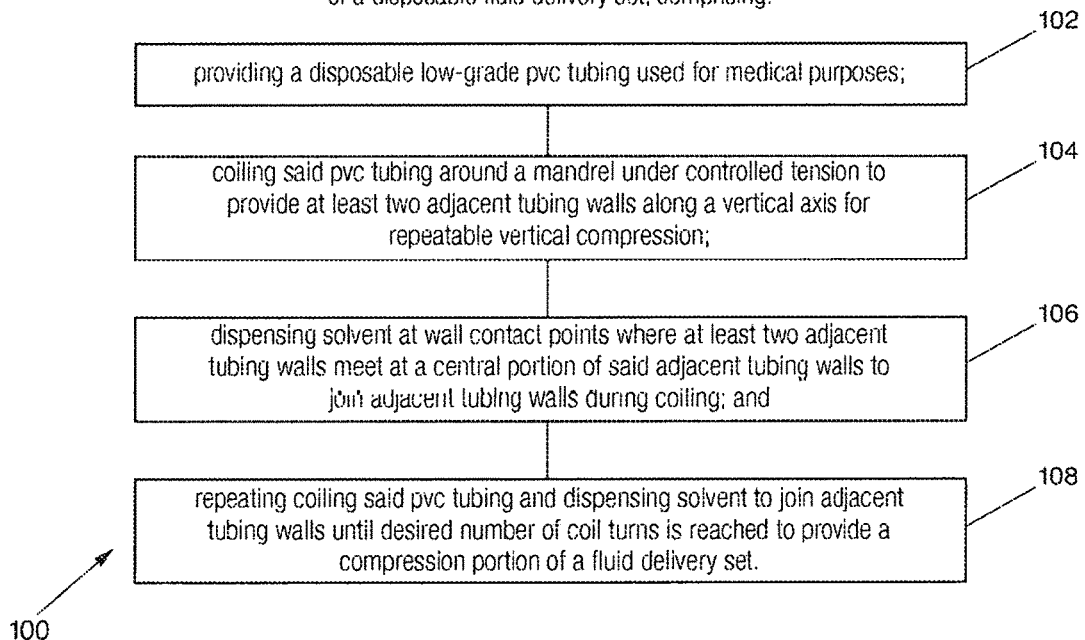
FIG. 9 is a block diagram of a method of manufacturing a repeatable compression portion of a disposable fluid delivery set.
Figure 10:
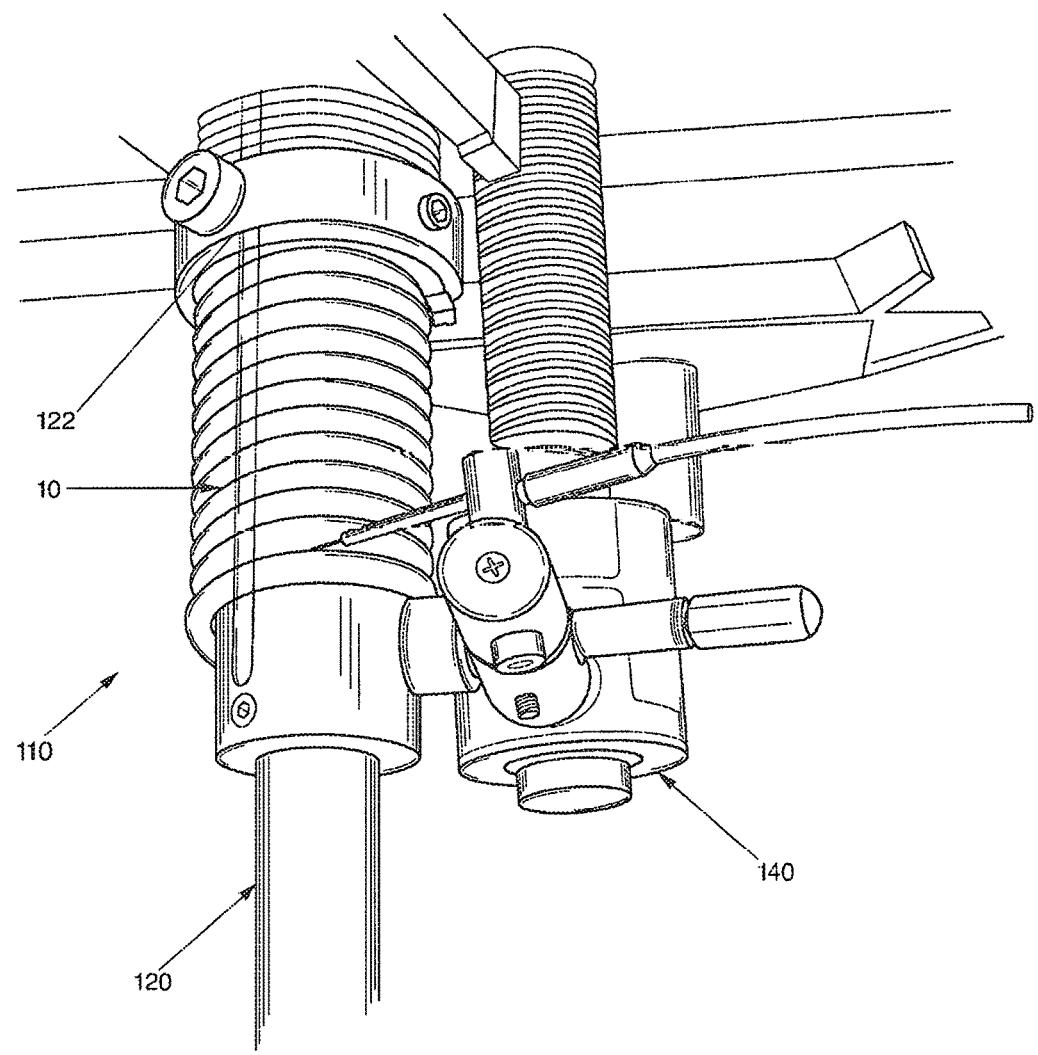
FIG. 10 is a top view of a coiling apparatus for producing a repeatable compression portion of a disposable fluid delivery set.
Figure 11A:
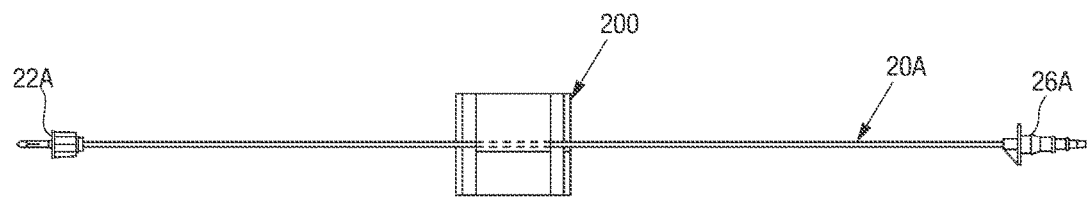
FIGS. 11A-11D are a sequence of side views of another embodiment including a disposable fluid delivery set having a portion inserted within a capture mechanism of an enteral feeding pump to provide a compression portion.
Figure 11B:
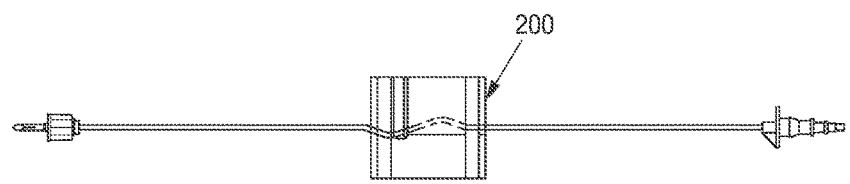
Figure 11C:
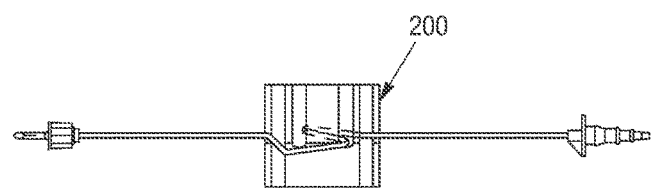
Figure 11D:
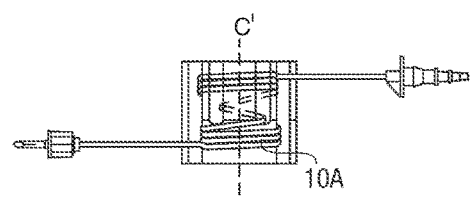
Figure 12A:
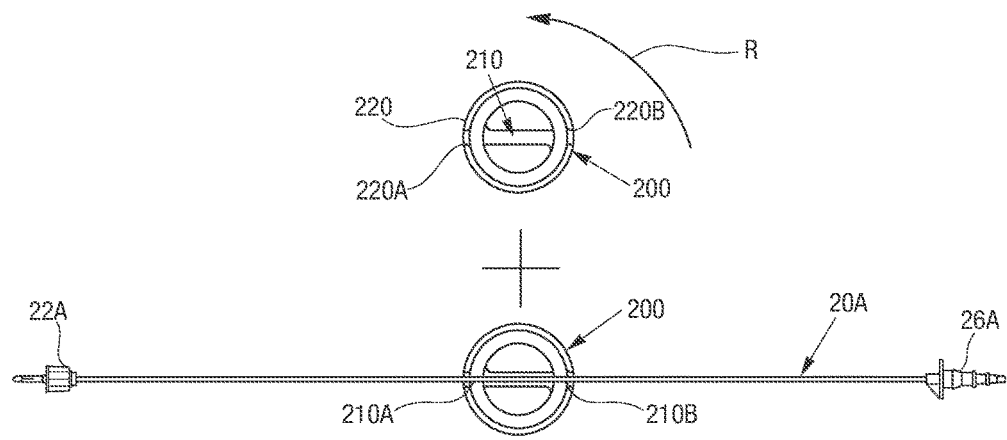
FIGS. 12A-12D are respective sequence of top views of the embodiment of FIGS. 11A-D showing the rotating of the portion of the tubing set within the capture mechanism to provide a compression portion.
Figure 12B:
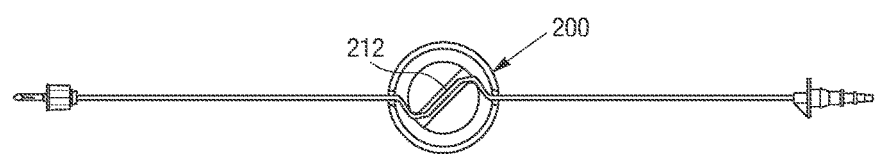
Figure 12C:
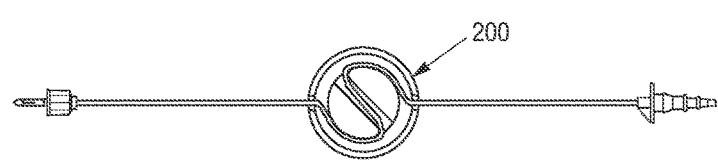
Figure 12D:
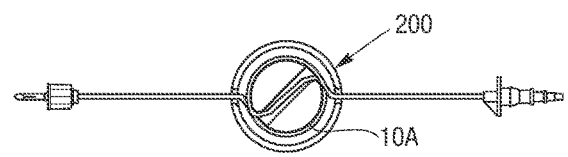

Referring to FIGS. 4-6, the enteral feeding pump 40 is configured to repeatedly and reliably compress the compression portion 10 of the fluid delivery set 20, 30 along a central axis C. The enteral feeding pump 40 including a housing 42, a pump motor unit 54 disposed within the housing 42, a controller 52 disposed within the housing 42 for directing the operation of the pump motor unit 54 to provide selective sequential compression, and a repeatable compression means for compressing the compression portion 10 of the fluid delivery set 20, 30.

In one embodiment, the repeatable compression means includes a plate system 44 driven by the pump motor unit 54 and disposed within the housing 42. The plate system 44 includes a top plate 44A respectively positioned to a bottom plate 44B. The top plate 44A and the bottom plate 44B configured to receive the compression portion 10 of a fluid delivery set 20, 30 with an interior portion of the top plate 44A and bottom plate 44B. The top plate 44A are operationally connected to the pump motor unit 54 to axially move the top plate 44A towards the bottom plate 44B.

The enteral feeding pump 40 may also include a regulation means for regulating the flow of medical fluid into and out of the compression portion 10 of the fluid delivery set 20, 30. In one embodiment, the means for regulating a flow of medical fluid are source end 46 and patient end 48 pinching mechanisms disposed within the housing 42 and operationally connected to the pump motor unit (not shown). The source end pinching mechanism 46 includes first source end 46A and second source end 46B pinching members. The first source end pinching member 46A respectively positioned to the second source end pinching member 46B. The first source end 46A and second source end pinching members 46B configured to receive a portion of a fluid delivery set 20, 30 between said source end 21B, 31B of the fluid delivery set 20, 30 and the compression portion 10 of the fluid delivery set 20, 30. The first source end pinching member 46A, second source end pinching member 46B, or both are operationally connected to the motor unit (not shown) to move the first source end pinching member 46A relatively towards said second source end pinching member 46B to squeeze or apply pressure to a portion of the fluid deliver set 20, 30 to regulate the flow of fluid through the fluid delivery set 20, 30 from a fluid source.

The patient end pinching mechanism 48 includes first patient end 48A and second patient end pinching members 48B. The first patient end pinching member 48A respectively positioned to the second patient end pinching member 48B. The first patient end 48A and second patient end pinching members 48B configured to receive a portion of the fluid delivery set 20, 30 between the patient end 21A, 31A of the fluid delivery set 20, 30 and the compression portion 10 of the fluid delivery set 10. The first patient end pinching member 48A, second patient end pinching member 48B, or both operationally connected to the pump motor unit 54 to move the first patient end pinching member 48A relatively towards the second patient pinching member 48B to squeeze or apply pressure to a portion of the fluid delivery set 20, 30, which regulates the flow of fluid through the fluid delivery set 20, 30 and to the patient.

When the pinching members 46A, 46B, 48A, 48B apply enough pressure when engaging a portion of the fluid delivery set 20, 30, the flow of liquid is "pinched off" to prevent the flow of fluid through either the patient end 21A, 31A, source end 21B, 31B, or both. This is called a closed position. When the pinching members 46A, 46B, 48A, 48B reduce or eliminate the pressure on the portion of the fluid delivery set 20, 30, the flow of liquid is allowed to return through either the patient end 21A, 31A, source end 21B, 31B, or both. This is called an open position.

Referring to FIG. 5, a block diagram 50 depicts the key components of the enteral feeding pump 40. A controller 52 is in electrical communication with the pump motor unit 54 to direct the selective sequential compression. The pump motor 54 is operationally connected with the plate system 57 and the pinching mechanisms 58, 59. Upon direction from the controller 52, the pump motor 54 drives the plate system 57, source end pinching mechanism 58, and patient end pinching mechanism 59 in selective sequential compression described further herein to provide unidirectional flow of liquid through a fluid delivery set 20, 30. The controller 52, pump motor 54, and power source 56 and methods of communication therebetween are known in the art.

In another embodiment, the means for regulating a flow of medical fluid into and out of the compression portion 10 of the fluid delivery set 20, 30 includes two or more valves 72, 74 fluidly connected at a patient end 21A, 31A and source end 21B, 31B of the fluid delivery set 20, 30. For example, a source end one-way valve 74 is fluidly connected between the source end 21B, 31B and the compression portion 10 of the fluid delivery set 20, 30. In addition, a patient end one-way valve 72 fluidly connected between the patient end 21A, 31A and the compression portion 10 of the fluid delivery set 20, 30. The valves 72, 74 are preferably one-way valves or other valves which in combination allow fluid to flow unidirectionally.

In operation, the compression portion 10 is repeatably compressed without distortion along a central axis C by the enteral feeding pump 40 to flow fluid unidirectionally through the fluid delivery set 20, 30 using selective sequential compression. In one embodiment using the pinching mechanisms 46, 48, when the patient end pinching mechanism 48 is in an open position, the compression portion 10 is compressed or stroked into a compression position to allow the fluid to flow out of the compression portion 10 and through the patient end 21A, 31A. Next, the patient end pinching mechanism 48 is placed in a closed position and the source end pinching mechanism 46 is placed in an open position. The compression portion 10 then rebounds from the compressed position to draw fluid through the source end 21B, 31B and into the compression portion 10. The amount of rebound is a function of the tubing grade, quality and the degree of tubing compression characteristics. Note, this selective sequential compression may be adjusted using different predetermined timing sequences to increase or decrease the desired flow rate and volume of fluid delivered to the patient.

Another means to create directed flow is to use the patient end and source end pinching mechanisms 46, 48 in the remaining uncoiled tubing 21, 31 near both ends of the compressed portion 10. The two pinching mechanisms 46, 48 alternately open and close in concert, or selective sequential compression, with the compression portion cycles. The following sequence produces unidirectional flow:
0) patient pinch mechanism close
1) source pinch mechanism open
2) compressing portion release
3) source pinch mechanism close
4) compressing portion compress
5) patient pinch mechanism close
6) source pinch mechanism open
7) compressing portion release
8) source pinch mechanism close
9) patient pinch mechanism open . . . etc Fluid flow may be also directed by the inclusion of one way valves 72, 74 in the remaining uncoiled tubing 21, 31 near both ends of the compression portion 10. With a series of compressions and releases, fluid alternately forces one valve to open and another valve to close. The result is unidirectional flow. In operation, the compressing portion 10 moves along a central C or vertical axis for fluid to flow unidirectionally within the fluid delivery set 20, 30, when the compressing portion 30 is in a compressed position, the fluid is forced out of the fluid delivery set through a first valve 72 at the patient end, when the compressed portion 10 rebounds from the compressed position, fluid is drawn into the fluid delivery set through a second valve 74 at the source end.

The invention also includes a method for flowing fluid unidirectionally using an enteral pumping system including a disposable fluid delivery set and enteral feeding pump for delivery medical fluids 80. The method includes the following steps. First, a fluid delivery set is provided which includes a source end, a patient end, and the repeatable compression portion 82. Second, the enteral feeding pump is provided for repeatable compressing of the compression portion and regulating the flow of fluid into and out of the compression portion 84. Third, the fluid delivery set is inserted into the enteral feeding pump 86. In one embodiment, the fluid delivery set is color coded to mark the orientation of the compression portion within the enteral feeding pump. Fourth, the repeatable compression portion of the fluid delivery set is compressed using the enteral feeding pump 88. Fifth, a regulating means closes the flow of medical fluid out of the compression portion and into the patient end using the enteral feeding pump 89. Sixth, a regulating means opens the flow of medical fluid into the compression portion from the source end using the enteral feeding pump 90. Seventh, the compressed portion is released using the enteral feeding pump to allow medical fluids to be drawn into the fluid delivery set through the regulating means and into the compression portion from the source end 92. Eighth, the regulating means closes the flow of medical fluid into the compression portion from the source end using the enteral feeding pump 94. Ninth, the compressing portion is compressed by the enteral feeding pump to move medical fluids out of the compression portion, through the regulating means, and into the patient end 96. This process is continued depending upon the flow rate and volume of liquid desired for a patient.

In another embodiment, the invention also may provide a method for fluid flowing unidirectionally using the enteral feeding pump system. First, the method provides an enteral feeding pump system containing replaceable low-grade PVC tubing set having a source end and a patient end. The source end is connected to a fluid source and the patient end is connected to a patient. The compression portion of the PVC tubing set is configured in a coiled or cylindrical shape. The PVC tubing is coiled to provide at least two tubing walls of the PVC tubing stacked along a vertical axis. The tubing walls of the compressing portion are joined together by solvent welding. The compressing portion fluidly connected between the source end and the patient end. The first valve is connected to the patient end and a second valve connected to the source end. Second, the valve is closed at the patient end. Third, the valve is opened at the source end. Fourth, the compressing portion is released to allow fluid to be drawn into the tubing set through the second valve at the source end. Fifth, the valve at the source end is closed. Sixth, the compressing portion is compressed to move fluid out of the tubing set through the first valve at the patient end. Seventh, the valve is closed at the patient end. Eighth, the valve is opened at the source end. It has consistent geometry and the method of bonding adjacent turns results in minimum impact on the compression characteristics of the coil.

The present invention also includes a method of manufacture of a repeatable compression portion of a disposable fluid delivery set 100. The compression portion of a disposable fluid delivery set may be produced by the following steps for solvent welding. First, a disposable tubing is provided that is used for medical purposes 102. Second, the tubing is helically coiled around a central axis to define a cylindrical shape. Third, the tubing is tensioned and properly pitched during coiling to provide at least two adjacent tubing walls around the central axis for repeatable compression 104. In one embodiment, the tension on the tubing is provided by a weight of 250 gm and a pitch of 2.4 coils/cm. This is merely an example of the weight and pitch that can be used. Fourth, a dispensing solvent is applied at wall contact points where at least two adjacent tubing walls meet at a central portion of said adjacent tubing walls to join adjacent tubing walls during coiling 106. Fifth, the tubing is coiled under tension and joined by dispensing solvent to join adjacent tubing walls until desired number of coil turns is reached to define a cylindrical shape of the compression portion of the fluid delivery set 108. In an alternative embodiment, the solvent may be applied by dipping a compression portion in a solvent dipping bath to join the tubing walls together. The number of turns for the compression portion is variable depending upon the desire volume displaced upon a stroke.

The invention also includes a coiling apparatus 110 for producing a repeatable compression portion 10 of a disposable fluid delivery set 20, 30. The coiling apparatus includes a spinning mandrel 120 and a solvent dispenser 140. The mandrel 120 and solvent dispenser 140 having a power source, a motor unit for turning the mandrel, a controller for directing the operation of the motor unit and controller, and a solvent source. The mandrel is configured for helically coiling a disposable tubing under controlled tension to produce a compression portion 10 of the tubing defining a cylindrical shape. The mandrel 120 includes a retaining means 122 for the tubing on the mandrel during coiling. A solvent dispenser 140 is positioned near said mandrel 120 to contact the compression portion 10 of the tubing. The dispenser 140 is in fluid connection with a solvent source. The dispenser 140 provides a solvent to join wall contact points of adjacent tubing walls of the compression portion 10 during helical coiling of the tubing. The production of the compression portion 10 using the method and coiling apparatus 110 above result in a consistent coil diameter which is critical. The end result is compression portion which has coil turns bonded by the solvent weld effect. The main advantage of this is there is no additional material introduced that could distort the compression characteristics of the coil (as would occur if an adhesive were used).

The compression portion 10 is helically coiled around the central axis C. During engagement with the enteral feeding pump 40, the compression portion 10 is stroked or displaced along the central axis C. As shown generally in the FIGS. 1-10, the central axis C of the compression portion 10 is defined as a vertical axis or oriented at a 90 degree angle. However, it is contemplated that the central axis C of the compression portion 10 may be defined as a horizontal axis or oriented at a 180 degree angle or somewhere in between. To accommodate the stroking of the compression portion 10 at a 180 degree angle or along a horizontal axis, the enteral feeding pump 40 may have a plate system 44 which is oriented along a horizontal axis and the top and bottom plates 44A, 44B may include a retaining member or other means for seating the compression portion 10 within the top and bottom plates 44A, 44B.

In view of the foregoing, a new and novel enteral feeding pump system 60, 70 is provided which provides compression using a low cost tubing set for unidirectional flow of fluid. The enteral feeding pump system 60, 70 meets flow demand while not stressing other mechanical components. Also, the enteral pumping system has low grade tubing, which costs less than high grade PVC tubing, and does not contain associated hardware that adds cost to an enteral pumping system.

Referring to FIGS. 11A-D and 12A-D, in another embodiment, a repeatable compression portion 10A of the tubing set or disposable fluid delivery set 20A may be formed or created in-situ within the enteral feeding pump system. It should be noted that the embodiment and method disclosed in FIGS. 11A-D and 12A-D incorporate the advantages and benefits of the embodiments described above and in FIGS. 1-10. In this embodiment, the repeatable compression portion 10A of the set may be formed or created in-situ within a capture mechanism 200 of the enteral feeding pump using the tubing set 20A with a straight or linear portion of the tubing set which shall be described in more detail below.

The disposable fluid delivery set 20A for use with an enteral feeding pump to deliver medical fluids unidirectionally includes a disposable tubing used for medical purposes having a source end and a patient end. The tubing includes the repeatable compression portion 10A. The repeatable compression 10A portion is helically coiled within the capture mechanism 200 of an enteral feeding pump to define a cylindrical shape. The compression portion 10A is configured to pump a large volume of medical fluids per stroke from a source end and to a patient end. In one embodiment, the compression portion 10A includes at least two adjacent tubing walls joined around a central axis $C^1$ for repeatable compression.

The capture mechanism 200 of an enteral feeding pump may provide or create in-situ—the repeatable compression portion 10A of disposable fluid delivery set for use with an enteral feeding pump to deliver medical fluids unidirectionally. In one embodiment, the capture mechanism 200 has a housing 220 with one or more apertures 220A, 220B for initial receipt a straight or linear portion of the tubing set 20A. Of course, it is contemplated that the capture mechanism may have be a separate component, with its own housing, or share a common housing or portion thereof of the enteral feeding pump system. A reeling mechanism 210 is connected within the housing 220 and operationally connected to the enteral feeding pump for control of operations. The enteral feeding pump used with the capture mechanism is similar to the enteral feeding pump described above.

The reeling mechanism 210 has an inner area and an outer area. The reeling mechanism 210 has one or more apertures 210A, 210B within the outer area for initial receipt of the portion of the tubing set. The inner area defines a channel 220 for receipt of the portion of the tubing set to secure the tubing set within the capture mechanism 200. In one embodiment, the channel 220 extends entirely through the inner area of the reeling mechanism 210 for receipt of sufficient portion of the tubing set to secure it therein. The reeling mechanism 210 is configured to rotate about an axis C' with the tubing set therein. When it rotates, the reeling mechanism 210 provides the repeatable compression portion 10A by helically coiling the portion of the tubing set about a central axis C' and forming the required compression portion in-situ.

The repeatable compression portion 10A of the tubing set for use in enteral feeding pumps may be prepared by the following steps. First, a tube section, preferably linear or straight, of the tubing set is placed, inserted, engaged, introduced or otherwise within the capture mechanism. The capture mechanism 200 is operationally connected to the enteral feeding pump. Of course, the tubing set maybe made of flexible, low-grade PVC tubing along its entire length or other types of materials suited for enteral feeding. The straight, flexible tube section is terminated at each end by suitable connectors for a patient end and a fluid end.

Next, the tube section is reeled, coiled, rotated or otherwise within the capture mechanism 200 around a central axis C' to provide a helically coiled section defining a cylindrical shape and forming the compression portion of the tubing set within the capture mechanism. To remove the compression portion and the tubing set from the capture mechanism, the capture mechanism may be reverse its original direction.

Once the process of forming the compression portion 10A within the capture mechanism 200 is complete, the enteral pump may reconfigure itself to produce oscillatory motion that would compress and release the compression portion thus causing fluid flow. Of course, it is contemplated that other means for compressing the compression portion disclosed above, such as the plate system, may also be used in conjunction with the capture mechanism.

The capture mechanism 200 may be incorporated within the enteral pump system which includes the disposable fluid delivery set, an enteral feeding pump, and a means for a means for repeatable compressing of a compression portion of a fluid delivery set. In operation, the compression portion repeatably compresses along a central axis for fluid to flow unidirectionally through the fluid delivery set. When the compressing portion is in a compressed position, the fluid is forced out of the fluid delivery set through the patient end, and when the compression portion rebounds from the compressed position, fluid is drawn into the fluid delivery set through the source end.

Directional flow may be achieved by incorporating one-way valves in both tubing connectors. The proximal connector 22A, connecting to the fluid source, would have a low cracking pressure check or duck-bill valve. The distal connector 26A, connecting to the patient access tube, would have another one-way valve designed with a cracking pressure sufficient to prevent unwanted flow due to normal head pressure. Pressure produced by the coil compression would exceed the cracking pressure and fluid would flow from the source container to the patient. Varying the oscillatory period and/or stroke would allow for flow rate adjustment. Again, the compression sequence for pumping using capture mechanism may be similar to the embodiments previously disclosed above.

The method of operation of the enteral feeding pump system incorporating the capture mechanism 200 may operate in accordance with the following steps but is merely an example and other methodologies of operation discussed above may be used. First, a fluid delivery set is provided having a source end and a patient end. Second, an enteral feeding pump is provided for regulating the flow of fluid into and out of the fluid delivery set. Third, a tube section of the tubing set made of low-grade PVC tubing is inserted within a capture mechanism operationally connected to an enteral feeding pump. Fourth, the tube section is reeled within the capture mechanism around a central axis to provide a helically coiled repeatable compression section of the tubing set within the capture mechanism. The repeatable compression portion of said fluid delivery set is compressed using the enteral feeding pump. A means for regulating the flow of medical fluid out of the compression portion and into the patient end using the enteral feeding pump is closed. A means for regulating the flow of medical fluid into the compression portion from the source end using the enteral feeding pump is opened. The compressing portion is released using the enteral feeding pump to allow medical fluids to be drawn into the fluid delivery set through the means for regulating the flow of medical fluid into the compression portion from the source end. The means for regulating the flow of medical fluid into the compression portion from the source end using the enteral feeding pump is closed. Next, the compressing portion is compressed using the enteral feeding pump to move medical fluids through the means for regulating the flow of medical fluid out of the compression portion and into the patient end.

It would be appreciated by those skilled in the art that various changes and modifications can be made to the illustrated embodiments without departing from the spirit of the present invention. All such modifications and changes are intended to be within the scope of the present invention.

What is claimed is:

1. A method for flowing fluid to a patient, comprising:
providing a fluid delivery set having a source end and a patient end with a repeatable compression portion intermediate the ends;
providing an enteral feeding pump for regulating flow of fluid into and out of the fluid delivery set;
compressing the repeatable compression portion using the enteral feeding pump;
selectively closing a first flow of medical fluid out of the repeatable compression portion;
selectively opening a second flow of medical fluid into the repeatable compression portion from the source end, wherein in a rebound position, the first flow of medical fluid is closed and the second flow of medical fluid is open; and
releasing the repeatable compression portion in the rebound position to allow medical fluids to be drawn into the fluid delivery set from a source.

2. The method of claim 1, further comprising the step of inserting a portion of the fluid delivery set within a capture mechanism to form the repeatable compression portion.

3. The method of claim 2, further comprising the step of reeling in the portion within the capture mechanism around a central axis within the capture mechanism.

4. The method of claim 1, wherein the fluid delivery set is a disposable tubing set made of low-grade PVC tubing.

* * * * *